United States Patent
Fallon et al.

[11] Patent Number: 5,820,875
[45] Date of Patent: *Oct. 13, 1998

[54] DEVICE FOR ADMINISTERING DRUG TRANSDERMALLY WITH A CONTROLLED TEMPORAL CHANGE IN SKIN FLUX

[75] Inventors: Renee A. Fallon, Sunnyvale; Donald R. Wilson, San Francisco; Russell D. Beste, Mountain View, all of Calif.

[73] Assignee: Cygnus, Inc., Redwood City, Calif.

[ * ] Notice: The term of this patent shall not extend beyond the expiration date of Pat. No. 5,352,456.

[21] Appl. No.: 211,029

[22] PCT Filed: Oct. 9, 1992

[86] PCT No.: PCT/US92/08631

§ 371 Date: Mar. 16, 1994

§ 102(e) Date: Mar. 16, 1994

[87] PCT Pub. No.: WO93/06803

PCT Pub. Date: Apr. 15, 1993

Related U.S. Application Data

[63] Continuation-in-part of Ser. No. 775,638, Oct. 10, 1991.
[51] Int. Cl.$^6$ ..................................................... A61F 13/02
[52] U.S. Cl. ........................... 424/448; 424/449; 424/447
[58] Field of Search ..................................... 424/448, 449, 424/447

[56] References Cited

U.S. PATENT DOCUMENTS

| | | | |
|---|---|---|---|
| 4,060,084 | 11/1977 | Chandrasekaran et al. | 128/260 |
| 4,379,454 | 4/1983 | Campbell et al. | 604/897 |
| 4,460,372 | 7/1984 | Campbell et al. | 604/897 |
| 4,698,062 | 10/1987 | Gale et al. | 604/896 |
| 4,764,379 | 8/1988 | Sanders et al. | 424/449 |
| 4,814,168 | 3/1989 | Sablotsky et al. | 424/78 |
| 4,906,463 | 3/1990 | Cleary et al. | 424/78 |
| 4,927,632 | 5/1990 | Wong et al. | 424/422 |
| 4,956,181 | 9/1990 | Bayer et al. | 424/448 |
| 4,994,267 | 2/1991 | Sablotsky | 424/78 |
| 5,300,291 | 4/1994 | Sablotsky et al. | 424/78.18 |
| 5,352,456 | 10/1994 | Fallon et al. | 424/448 |

OTHER PUBLICATIONS

Comfort et al., "Biphasal transdermal drug delivery" *Proc. J. Intern. Symp. Control, Rel. Bioact. Mater.* (1991) 18:297–298.

Berner et al., "Ethanol: water mutually enchanced transdermal therapeutic system II: skin permeation of ethanol and nitroglycerin" *J. Pharm. Sci.* (1984) 78:402–407.

Kondo et al., "Enhancement of transdermal delivery by susperfluous thermodynamic potential. I. Thermodynamic analysis of nifedipine transport across the lipoidal barrier" *J. Pharm.–Dyn.* (1987) 10:587–594.

Kondo et al., "Enhancement of transdermal delivery by superfluous thermodynamic potential. III. Percutaneous absorption of nifedipine in rats" *J. Pharm.–Dyn.* (1987) 10:743–749.

Coldman et al., "Enhancement of percutaneous absorption by the use of volatile: nonvolatile systems as vehicles" *J. Pharm. Sci.* (1969) 58:1098–1102.

Kondo et al., "Enhancement of transdermal delivery by superfluous thermodynamic potential. II. In vitro–in vivo correlation of percutaneous nifedipine transport" *J. Pharm.–Dyn.* (1987) 10:662–668.

*Primary Examiner*—Frederick Krass
*Attorney, Agent, or Firm*—Morrison & Foerster LLP

[57] ABSTRACT

A transdermal drug delivery device that administers drug in an initial pulse followed by a substantially lower continuous rate comprising a drug reservoir of the drug dissolved in a nonvolatile skin permeation enhancer and a volatile permeation enhancer confined between a backing that is permeable to the volatile permeation enhancer and an underlying substrate layer that is permeable to the drug and both enhancers. When the device is placed on the skin the volatile permeation enhancer is depleted from the reservoir by evaporation through the backing such that the magnitude and duration of the pulse is dependent upon the permeability of the backing layer to the volatile enhancer.

29 Claims, 6 Drawing Sheets

1

DEVICE FOR ADMINISTERING DRUG TRANSDERMALLY WITH A CONTROLLED TEMPORAL CHANGE IN SKIN FLUX

This application is a national filing under 35 U.S.C. § 371, of international application PCT/US92/08631, filed Oct. 9, 1992, which in turn is a continuation in part of U.S. Ser. No. 07/775,638, filed Oct. 10, 1991, now U.S. Pat. No. 5,352,456, issued Oct. 4, 1994, the contents of each incorporated by reference.

DESCRIPTION

1. Technical Field

This invention is in the field of medical devices for administering drugs transdermally. More particularly, it concerns a transdermal drug delivery device whose structure and composition is such that the skin flux of the drug varies in a controlled manner over the period of administration, typically from a high flux in the initial stage of administration to a lower flux in the later stage of administration.

2. Background

The efficacy of some systemically acting drugs may be optimized by administering them in a manner that produces therapeutically effective blood levels rapidly. The most common such method of administration is bolus injection. Oral administration, depending upon the ability of the drug to be absorbed into circulation via the gastrointestinal tract, may also afford a rapid onset of therapeutically effective blood levels.

Transdermal drug delivery, while often viewed as an advantageous mode of administration over injection or oral dosing, is not normally considered to be a practical means for achieving high blood levels of drug rapidly. This is because most transdermal devices operate in a manner that results in a significant lag time between placing the device on the skin and realizing the required or desired blood levels.

There are, however, two prior transdermal device designs that have been proposed for providing an initial burst or pulse of drug. The first of these designs is described in U.S. Pat. No. 4,060,084. It involves use of a drug reservoir layer in which the bulk of the drug is contained, an underlying rate-controlling membrane that controls the release rate of the drug from the reservoir, and a basal adhesive layer that is loaded with drug. When this type of device is placed on the skin, the drug in the adhesive migrates rapidly into the skin providing a "burst." The burst is followed by the controlled delivery of drug from the reservoir via the rate-controlling membrane. The second design is described in U.S. Pat. No. 4,698,062. It uses a first reservoir which contains a sufficient amount of the drug to provide a baseline flux over the entire administration period and a second reservoir which contains a permeation enhancer in an amount that is sufficient to provide enhancement only during the beginning of the administration period. With this design, the magnitude and duration of the period of enhanced drug flux is apparently dependent only upon the amount of enhancer contained in the second reservoir and its effect on skin flux. The patent indicates that this pattern of drug release may be achieved with various enhancers including ethanol, n-decylmethylsulfoxide, dimethyl lauramide, and polyethylene glycol monolaurate.

Prior workers have investigated certain aspects of transdermal drug delivery from binary solvent systems. Comfort et al., Proc. J. Intern. Symp. Control. Rel. Bioact. Mater. (1991) 18:297–298, describes the release of nitroglycerin through cadaver skin from solutions of nitroglycerin in mixtures of ethanol and water. Berner et al., J. Pharm. Sciences (1984) 78:402–407, also described the flux of nitroglycerin through skin from ethanol/water solutions. Their studies show that ethanol flux from the solution is a function of the ethanol/water ratio, with a maximum occurring at a ratio of 0.5:1 and that nitroglycerin flux is a linear function of ethanol flux. Kondo et al., Pharmaco. Ber. (1987) 10:587–594 and 743–749, report studies relating to the delivery of nifedipine through an ethylene-vinyl acetate membrane and skin from mixtures of acetone and propylene glycol and/or isopropyl myristate. They observed a transient increase in the flux of nifedipine from such mixtures which they attributed to the evaporation of the acetone from the mixture. They further teach adding polymeric agents to the solution to prevent the nifedipine from precipitating from the solution. Finally, Coldman et al., J. Pharm. Sciences (1969) 58:1098–1102, show that the 16 hour cumulative transdermal delivery of fluocinolide from a binary mixture of isopropyl alcohol and isopropyl myristate is a function of the ratio of the two solvents and that maximal flux occurs at a ratio of 4:1.

Accordingly, prior investigators have shown that the transdermal flux of drugs from mixed solvents may be a function of the ratio of the individual solvents in the mixture. However, none of the prior investigators suggested transdermal devices which include means for changing the ratio of the individual solvents relative to one another in a controlled manner to thereby alter the flux in a controlled manner. The present invention employs such means.

DISCLOSURE OF THE INVENTION

The present invention is a device for administering a drug through an area of intact skin over an administration period wherein the flux of drug through said area varies temporally in a controlled manner comprising:

(a) a reservoir comprising said drug dissolved in a solvent mixture comprising a first solvent and a second solvent in a predetermined weight ratio, wherein at least one of the solvents is a skin permeation enhancer and said flux is a function of the weight ratio of the first solvent to the second solvent in the reservoir;

(b) means for effecting controlled differential transport of one of said first and second solvents relative to the other from the reservoir during said administration period whereby the weight ratio of the first solvent to the second solvent in the reservoir is changed in a controlled manner and thus said flux is changed in a controlled manner; and (c) means for maintaining the device in drug and solvent transferring relationship with said area of skin.

Another aspect of the invention is a method for administering a drug transdermally through an area of intact skin over an administration period wherein the flux of drug through said area varies temporally on a controlled manner comprising:

(a) applying a formulation of the drug dissolved in a solvent mixture comprising a first solvent and a second solvent in a predetermined weight ratio, wherein at least one of the solvents is a skin permeation enhancer and the formulation is covered by a backing that is peremable to the volatile solvent; and (b) permitting the volatile solvent to evaporate from said formulation through said backing whereby the magnitude and duration of the pulse is determined by inter alia the permeability of the backing to the volatile solvent.

MODES FOR CARRYING OUT THE INVENTION

Figure 1:
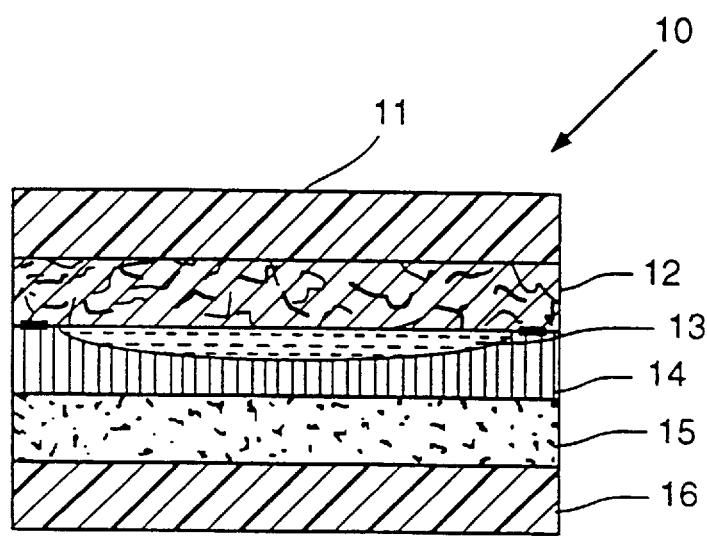
FIG. 1 is an elevated cross-section (not to scale) of one embodiment of the invention.

As used herein the term "drug" intends a biologically active compound or mixture of compounds that is capable of diffusing through skin with or without the assistance of skin permeation enhancers and which has a therapeutic, prophylactic or other beneficial effect on the wearer of the device. Drugs whose efficacy is facilitated by being administered in a manner that provides therapeutically effective blood levels rapidly are particularly adapted for use in the invention. Examples of such drugs are: sedatives, hypnotics and anti-anxiety agents such as diazepam, midazolam, lorazipam and alprazolam; barbiturates such as pentobarbital, and secobarbital; antihistamines such as hydroxyzines, diphenhydramine, phenothiazine, promethazine and propiomazine; buterophenones such as droperidol; opioids such as morphine, meperidine, fentanyl, sufentanyl, and alfentanyl; antiemetics such as droperidol, hydroxyzine, benzquinamide, scopolamine, and cyclizine; anticholinergic drugs such as atropine, scopolamine, and glycopyrrolate; and alpha 2 agonists such as clonidine and dexmedetomidine.

As used herein the term "flux" intends the rate of transfer of drug across skin as measured by the in vitro human cadaver skin tests described in *Medical Device and Diagnostic Industry* (1985) 8:35–42. The units of flux are preferably $\mu g/cm^2/hr$.

The term "volatile" that is herein used to describe certain solvents and permeation enhancers used in the invention intends compounds that have a vapor pressure greater than about 10 mm Hg at 25° C., preferably greater than about 30 mm Hg at 25° C. Correspondingly, the term "nonvolatile" that is used herein to describe certain other solvents that may be used in the invention intends compounds that have a vapor pressure less than about 5 mm Hg at 25° C., preferably less than about 1 mm Hg at 25° C.

As used herein the term "initial pulse" intends a transient increase in flux relative to the baseline flux that is realized via administration of the drug from a monolithic matrix composed of the drug dissolved in a nonvolatile carrier. Such increase will usually be five-to ten-fold greater than said baseline flux. Correspondingly, the term "substantially" lowers as used to characterize the flux after the initial pulse intends a flux that is typically 1% to 30%, more usually 10% to 20% of the maximum flux reached during the initial pulse. The initial pulse will normally last 0.5 to 8 hrs, more usually 1 to 4 hrs. The duration of the initial pulse in the flux will normally constitute 1% to 35%, more usually 10% to 20% of the administration period.

As used herein the term "administration period" intends the time period over which the device will deliver the drug at a rate that achieves and maintains the therapeutic, prophylactic or beneficial effect for which the drug is indicated. The administration period will usually be 1 to 7 days, more usually 1 to 3 days.

The term "reservoir" as used herein is intended to broadly denote the element of the device where the principal store of drug resides. This term is intended to include, without limitation, a walled or otherwise confined space in which the solution of drug resides and a layer or multiplicity of layers in the form of a matrix comprised of a dispersion, suspension or other mixture of the drug solution in one or more polymers. Such latter type reservoirs are often referred to as a "monolithic" structure in the transdermal art.

In the transdermal devices of the invention the drug is present in the form of a solution in a mixture of at least two solvents, one of which is a skin permeation enhancer, and the flux is a function of the weight ratio of the individual solvents in the mixture. The equilibrium absorption of the solvents into skin is likewise dependent upon that ratio. Further, the maximum drug flux from such a solvent mixture occurs at the weight ratio that maximizes partitioning of the solvents into the skin. That ratio may be determined experimentally using conventional equilibrium absorption studies on mixtures of the solvents. For instance, such studies on the ethanol:propylene glycol monolaurate binary show the maximum occurs at a weight ratio of approximately 4:1. Thus, in instances where it is desirable to administer the drug in an initial pulse or burst, the weight ratio of solvents that produces maximum drug flux or a ratio approximating the same (e.g., ±20%) will typically be used.

The devices of the invention also include means that cause differential transport of the individual solvents from the reservoir during the functional lifetime of the device. In this regard, depending upon the volatility of the solvents and the structure of the device (i.e., whether it is occlusive), they may be transported from the reservoir into the atmosphere by evaporation. Alternatively, depending upon the permeability of structure underlying the reservoir and the permeability of the skin to the solvents, they may be transported by diffusion from the reservoir and into the skin at differential rates. In yet another alternative, the differential transport may be due to a combination of differential evaporation of the solvents from the reservoir to the atmosphere and diffusion of the solvents from the reservoir into the skin at different rates. Typically, the means for achieving such differential transport of the solvents from the reservoir will be one or more layers or membranes overlying the reservoir that control the rate of evaporation of at least one of the solvents to the atmosphere and/or one or more layers or membranes underlying the reservoir that control the rate of diffusion of at least one of the solvents from the reservoir and into the skin.

FIG. 1 depicts one embodiment, generally designated 10, of the invention device. Device 10 is designed to release drug in an initial pulse followed by a lower flux. It is structured to effect differential transport of a volatile solvent from the top or face surface of the device. Device 10 is in the form of a laminated composite having six components: (1) an uppermost impermeable backing layer 11 which forms the top surface of the device and which is removed from the device at the time the device is applied to the skin; (2) a permeable backing layer 12 that defines the top surface of the device during the administration period; (3) a confined drug reservoir 13 composed of a solution of drug in a nonvolatile solvent/permeation enhancer and a second solvent/permeation enhancer; (4) a permeable substrate layer 14 that is sealed to the backing layer 12 about the periphery of the reservoir 13; (5) a pressure-sensitive adhesive layer 15; and (6) a release liner layer 16 that is removed prior to placing the device on the skin.

The purpose of impermeable backing layer 11 is to prevent the volatile permeation enhancer from evaporating from the top of the device during storage. (The release liner layer plays a corresponding role at the opposite basal face of the device.) Accordingly, this layer is made of a material or combination of materials that is substantially impermeable to the volatile enhancer and, preferably, the other components of the reservoir as well. It must also be capable of being removed from the remainder of the device so as to expose the underlying permeable backing 12 to the atmosphere. Examples of materials from which layer 11 may be made are metal foils, polycarbonate, polyesters, polytetrafluoroethylene, and polypropylene. The thickness of layer 11 is not critical. Its thickness will normally be in the range of 1 to 20 mm.

In an alternative embodiment of the invention, the impermeable backing may be eliminated by packaging the device so that the space within the package contains a sufficient amount of the volatile enhancer in vapor form to prevent the volatile enhancer in the reservoir from evaporating. In other words, the volatile enhancer vapor within the package is in equilibrium with the liquid form of the enhancer within the reservoir. In another alternative embodiment, the impermeable backing may be provided as an integral component of the package such that when the device is removed from the package the backing is left behind.

Permeable backing 12 underlies layer 11. As indicated, when layer 11 is removed, the thus exposed upper surface of layer 12 defines the top surface of the device. Backing layer 12 is sufficiently permeable to the volatile enhancer contained within the reservoir so as to permit essentially complete evaporation of the enhancer to occur within 0.1 to 10 hours, more usually 0.1 to 1 hour, from the time at which the impermeable backing and release liner are removed from the device and the device is placed on the skin.

Preferably layer 12 does not substantially absorb the drug or the other components of the reservoir while being permeable to the volatile enhancer. Layer 12 may be made from a dense (substantial absence of micro- or macropores) continuous material or from a porous or fibrous (e.g., nonwoven fabric) material that is capable of being sealed, preferably heat sealed, to the underlying substrate layer about the periphery of the reservoir. Preferably it is made of a polymeric material. Examples of dense or porous polymer films from which layer 12 may be made are microporous polyester and polyethylene. When dense or porous materials are used the thickness of layer 12 will typically be between 1 and 10 mm, more usually 2 to 5 mm. An example of a fibrous material from which the layer may be made is nonwoven polyester. Since layer 12 is permeable, it is noted that this device is nonocclusive (i.e., it permits transport of moisture and gases to and from the skin surface).

The drug reservoir 13 is confined between overlying layer 12 and underlying layer 14. As indicated, the confinement may be accomplished by heat sealing layers 12 and 14 together about the periphery of the reservoir. The reservoir comprises the drug dissolved in a first nonvolatile solvent (the drug may be present in excess, at saturation, or below saturation) and, at the time of placement on the skin, the volatile solvent/permeation enhancer. The first solvent may also optionally be a nonvolatile permeation enhancer. As indicated previously, to achieve a maximum pulse, the weight ratio of the first solvent to the second solvent is that ratio which maximizes partitioning of the two solvents into the skin.

As the volatile solvent selectively evaporates via the face surface of the device, the weight ratio of the two solvents in the reservoir change, thus causing the flux of the drug, which is a function of the solvent weight ratio, to change. The change in solvent composition may also cause the concentration of drug in the solvent mixture to change. Preferably the change in solvent mixture causes the concentration of drug in the solvent mixture to increase. A plot of drug flux from device 10 over time will show an initial pulse to drug followed by a substantially lower flux. The magnitude and duration of the pulse will depend upon the initial solvent weight ratio, the concentration of drug in the solvent mixture, the change in the solvent weight ratio over time, and the permeation enhancement effected by the solvent(s). In device 10 the change in solvent weight ratio depends on the volatility of the volatile solvent and the permeability of backing 12 to the volatile solvent.

The flux of drug from device 10 following the initial pulse will be sufficient to maintain therapeutically effective levels of the drug in circulation for the desired administration period. The magnitude of that flux will depend on the permeability of the skin to the drug. That permeability may be enhanced by one or more of the solvents.

The amount of drug in the reservoir will depend upon the required rate of release of drug from the device and the intended lifetime of the device. Accordingly, the particular amount will vary from drug-to-drug. Normally the drug will constitute 1% to 20%, more usually 5% to 15% by weight of the reservoir. Correspondingly, the volatile permeation enhancer will normally constitute 65% to 95% by weight of the reservoir, more usually 75% to 85% by weight of the reservoir.

Examples of nonvolatile solvents that are not permeation enhancers that may be used in the invention are mineral oil, propylene glycol, and silicone oil. Examples of solvents that are nonvolatile permeation enhancers are propylene glycol monolaurate (PGML), glycerol monooleate (GMO), oleic acid, and benzyl alcohol. The solubility of the drug in the solvent mixture will usually be in the range of 50 to 100 mg/ml, more usually 70 to 90 mg/ml.

Examples of volatile solvents that may be used in the reservoir are ethanol, isopropyl alcohol, ethyl ether, and acetone. Ethanol is preferred.

Substrate layer 14 merely serves as a structural layer to provide a basal wall that confines the reservoir. As such it is not a rate-controlling barrier to diffusion of drug from the reservoir to the skin. In other words, it is substantially more permeable to the drug than is the skin. Preferably it has an insignificant or no affect on release of drug from the reservoir to the skin. As indicated above, it is preferably made of a polymeric material that may be sealed to permeable backing 12 about the periphery of the reservoir. It is preferably made of a microporous material or a fibrous (e.g., nonwoven) material. Examples of such materials are nonwoven polyester, and microporous polyester or polypropylene. It is noted that the reservoir may be formulated as a nonflowable matrix (e.g., as a hydrogel). In such an instance a substrate layer is not required.

Pressure-sensitive adhesive layer 15 is the means by which the device is affixed to and maintained on the skin in a drug and permeation enhancer transferring relationship. Accordingly, the basal surface of layer 15 is in direct contact with the skin during use of the device and its area corresponds to the area of skin through which the drug passes. Like layer 14, layer 15 is not a rate-controlling barrier and has little, if any, affect on flux of drug or enhancer from the reservoir to the skin. It will normally be made of a drug-permeable polymer conventionally used as pressure-sensitive adhesives in transdermal drug delivery devices.

Examples of such adhesives are polysiloxanes, polyacrylates, plasticized ethylene-vinyl acetate copolymers, low molecular weight polyester block amide copolymers (e.g., PEBAX copolymers), polyurethanes, and rubbery polymers such as polyisobutene. If desired, this layer may also be loaded with drug.

In the embodiment of FIG. 1 substrate layer 14 and adhesive layer 15 provide a diffusive pathway for the drug and enhancer(s) to migrate from the reservoir to the skin. In alternative embodiments in which an in-line adhesive layer is not used (e.g., such as use of a peripheral ring of adhesive, an adhesive overlay, straps, or other affixation means) to maintain the device on the skin, only substrate layer 15 is the diffusive pathway from the reservoir to the skin and the surface area of it in contact with the skin corresponds to the area of skin through which the drug is administered to circulation. In this regard that area (whether provided by the adhesive layer or the substrate layer) will typically be in the range of 10 cm$^2$ to 100 cm$^2$, more usually 20 cm$^2$ to 60 cm$^2$.

The release liner layer 16 is made of a conventional drug/enhancer impermeable polymer film (e.g., polyester) that is inherently strippable or rendered so by techniques such as silicone or fluorocarbon treatment.

Figure 5:
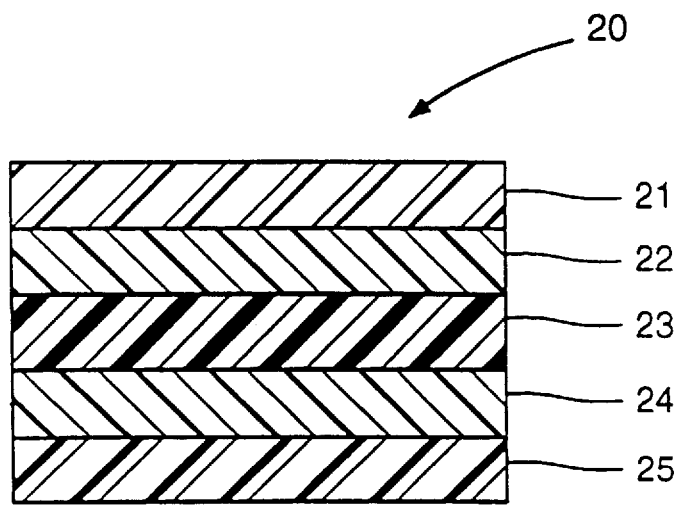
FIG. 5 is an elevated cross-section (not to scale) of another embodiment of the invention.

FIG. 5 illustrates another embodiment, generally designated 20, of the invention device. Device 20 is designed so that the drug reservoir is a "monolith" (i.e. a dispersion of drug solution in a polymer) and the differential transport of solvent from the device is controlled by a semipermeable membrane overlying the reservoir that controls the rate of evaporation of one of the solvents from the device as well as an underlying membrane that controls the rate of diffusion of the solvent(s) to the basal surface of the device.

Device 20 consists of a five layer laminated composite. The top or face surface layer 21 is a removable impermeable backing layer equivalent to layer 1 of device 10. Layer 21 is removed from the device at the beginning of the administration period. The next layer, designated 22, is a semipermeable membrane that defines the top surface of the device after layer 21 is removed. Below layer 22 is reservoir layer 23. Layer 23 is a multiphase dispersion. One phase of the dispersion is hydrophilic and comprises a hydrophilic polymer such as a polyaminoacrylate, polyvinyl pyrollidone, hydroxyethyl cellulose, or polyethylene oxide. The other phase of the dispersion is hydrophobic and comprises a hydrophobic polymer such as a solvent-based polyacrylate, polyisobutylene or polydimethyl siloxane. One or both types of polymers typically have pressure-sensitive properties. In most instances the drug solution will be associated with and part of the hydrophilic phase. Typically the hydrophilic polymer will constitute about 5% to 25% be weight of the total hydrophobic/hydrophilic polymer content of the layer and the hydrophobic polymer will constitute the remainder (75% to 95%). The solvent mixture will constitute about 5% to 50% by weight of the entire layer and the drug will constitute about 1% to 10% by weight of the entire layer.

Layer 23 may be formulated by mixing the solutions of the hydrophilic and hydrophobic polymers, casting the resulting mixture into a film and removing the solvent from the mix. The solution of drug in the solvent mixture is then sorbed into the film. Spreading of the solution in the film may be facilitated by applying a wicking layer (e.g. a porous or fibrous layer such as those described above) to the surface of the film. In order to avoid evaporation of the solvents, the solution covered film is itself covered or otherwise enclosed.

A second semipermeable membrane layer 24 lies immediately below reservoir layer 23. It together with semipermeable membrane 22 regulates the transport of the volatile solvent component of the solvent mixture from layer 23. Specifically, membrane 22 regulates the evaporation of the volatile solvent to the atmosphere and membrane 24 regulates the diffusion of the solvent from the reservoir to the skin. It will be appreciated that alternative embodiments of device 20 may be made in which membrane 24 is eliminated. In such embodiments, the solvent transport from the device is regulated solely by membrane 22. Semipermeable membrane materials are well known in the art and are exemplified by crosslinked silicone rubbers and polyurethanes. The bottom surface of membrane 22 functions as the basal surface of the device when the device is applied to the skin. Accordingly, it must have pressure sensitive adhesive properties or alternatively other means, such as an adhesive overlay or a peripheral adhesive layer, must be used to affix the device to the skin.

A conventional removable release liner layer 25 underlies layer 24. The release liner layer is removed before the device is applied to the skin.

The devices of FIGS. 1 and 5 may be made by conventional casting and lamination techniques. Commercially available films or nonwoven fabrics may be used for the impermeable backing, release liner, permeable backing and substrate layer and semipermeable membranes. Commercially available pressure-sensitive adhesives may be used to make the adhesive layer and the matrix layer in monolithic types of devices. The reservoir components may be formulated by conventional mixing procedures, using gelling agents, if necessary, to provide a formulation of desired physical properties.

The following examples further illustrate the invention. These examples are not intended to limit the invention in any manner.

EXAMPLE 1

This example shows the invention used to administer the drug alprazolam (marketed under the name Xanax) which is indicated for treatment of anxiety, depression, and panic disorders. Unless indicated otherwise, percentages are by weight.

Adhesive was prepared by mixing 5% propylene glycol monolaurate (PGML) and 0.5% Xanax in silicone 2920 (Dow Corning) adhesive. The adhesive was coated onto a fluorocoated release liner using an 8 mil (2 mm) fixed-gap gardner knife. The adhesive was dried for 30 min at 70° C. to remove the solvent. The adhesive was then laminated to a piece of Celgard 2400 (microporous polypropylene) which serves as the heat-seal substrate. This laminate is referred to as the contact laminate.

The reservoir fluid was prepared by mixing 80% ethanol with 15% PGML and 5% Xanax. A second control reservoir fluid was formulated by mixing 15% ethanol with 80% mixed vegetable oils (MVO, a mixture of natural soybean and coconut oils) and 3% Xanax. The mixtures were agitated until clear solutions were obtained.

The contact laminate was adhered to the skin for in vitro testing and the reservoir fluid was pipetted onto the top of the laminate. This mimics the effect of manufacturing a complete device or patch.

Modified Franz vertical cells were used for in vitro skin permeation studies which were carried out to determine the burst effect. The release liner was peeled off the system and the foil impermeable backing was also removed immediately prior to placing the system on heat-separated human epidermis. The epidermis and patch were then mounted between the donor and receiver compartments and clamped in place. The receiver compartments were filled with phosphate buffer and the temperature was maintained at 32° C. Samples were taken at preset intervals and assayed by HPLC.

Figure 2:
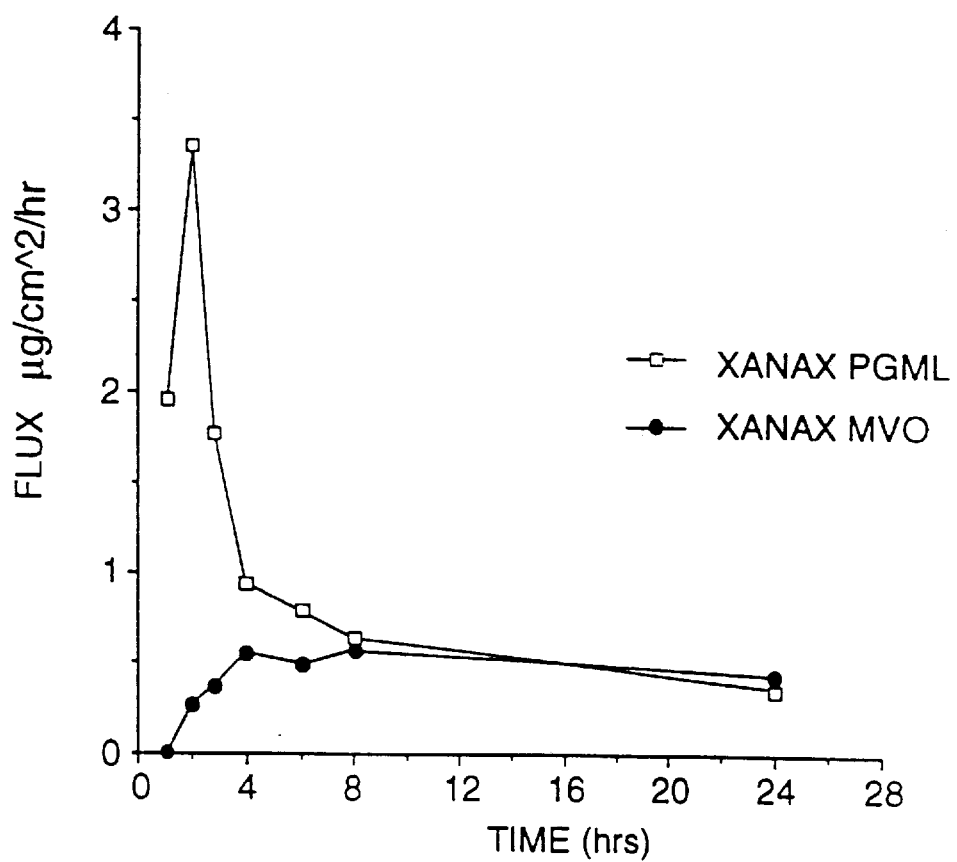
FIG. 2 is a graph showing the in vitro flux of xanax versus time, as determined pursuant to Example 1 infra.

The results of the tests are shown graphically in FIG. 2. As shown the invention device exhibited an initial pulse influx whereas the control device did not exhibit an initial pulse.

EXAMPLE 2

This example shows the use of the invention to deliver the drug dexmedetomidine.

Adhesive was prepared by mixing 5% PGML and 0.5% dexmedetomidine in silicone 2920 (Dow Corning) adhesive. The adhesive was coated onto a fluorocoated release liner using an 8 mil (2 mm) fixed-gap gardner knife. The adhesive was then laminated to a piece of Celgard 2400 (microporous polypropylene) which serves as the heat seal substrate. This laminate is referred to as the contact laminate.

The backing laminate was prepared by heat-laminating Reynolds foil 720 (1 mil foil with a heat-seal coating) to Reemay 2250 (nonwoven polyester). This heat seal is nondestructive, i.e., the materials may be separated without destroying them.

The reservoir fluid was prepared by mixing 80% ethanol with 20% PGML. One hundred mg/g of dexmedetomidine was added and the mixture was agitated until a clear solution was obtained.

The backing laminate is then destructively heat-sealed to the contact laminate (nonwoven in contact with the heat-seal substrate) around three sides of the patch. A 2-inch-by-1.5-inch piece of the nonwoven was placed into the patch through the open side to act as a sponge and hold the reservoir fluid (this has no effect on patch function but makes manufacturing easier). Two hundred ninety microliters of the reservoir fluid was pipetted into each patch through the open side. The open side is then heat-sealed closed to contain the fluid.

Figure 3:
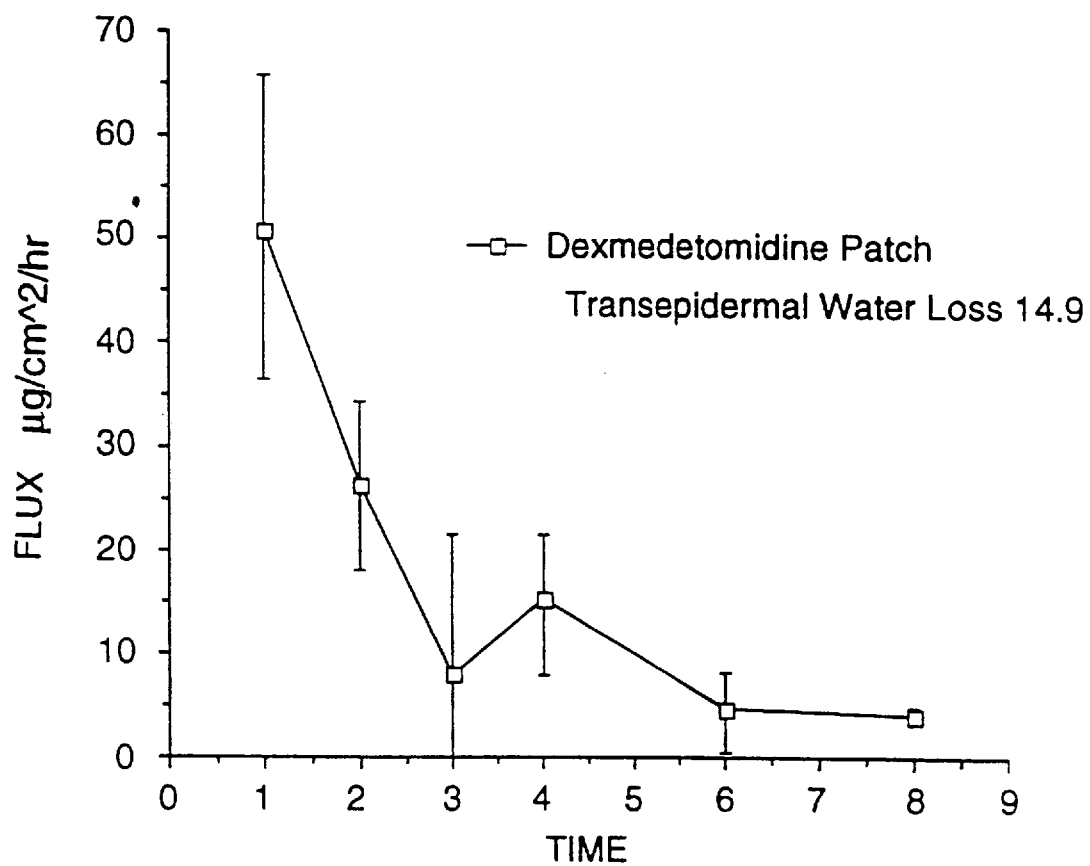
FIGS. 3 and 4 are graphs showing the in vitro flux of dexmedetomidine versus time, as determined pursuant to Examples 2 and 3 infra.

Modified Franz vertical cells were used for in vitro skin permeation studies which were carried out to determine the burst effect. The release liner was peeled off the system and the foil impermeable backing was also removed immediately prior to placing the system on heat-separated human epidermis. The epidermis and patch were then mounted between the donor and receiver compartments and clamped in place. The receiver compartments were filled with phosphate buffer, pH 5.0 and the temperature was maintained at 32° C. Samples were taken at preset intervals and assayed by HPLC. The results of these tests are shown in FIG. 3.

Modifications of the above-described modes for carrying out the invention that are obvious to those of skill in the fields of transdermal drug delivery devices are intended to be within the scope of the following claims.

EXAMPLE 3

This example also shows the use of the invention to administer desmedetomidine. As compared to Example 2, no drug or PGML was added to the adhesive layer in this example.

The adhesive was coated onto a fluorocoated release liner using an 8 mil (2 mm) fixed-gap gardner knife. The adhesive was dried for 30 minutes at 70° C. to remove the solvent. The adhesive was then laminated to a piece of Celgard 2400 (microporous polypropylene) which serves as the heat-seal substrate. This laminate is referred to as the contact laminate.

The backing laminate was prepared by heat-laminating Reynolds foil 720 (1 mil foil with a heat-seal coating) to Reemay 2250 (nonwoven polyester). This heat seal is nondestructive, i.e., the materials may be separated without destroying them.

The reservoir fluid was prepared by mixing 80% ethanol with 20% propylene glycol monolaurate. One hundred mg/g of dexmedetomidine was added and the mixture was agitated until a clear solution was obtained.

The backing laminate is then destructively heat-sealed to the contact laminate (nonwoven in contact with the heat-seal substrate) around three sides of the patch. A 2-inch-by-1.5-inch piece of the nonwoven was placed into the patch through the open side to act as a sponge and hold the reservoir fluid (this has no effect on patch function but makes manufacturing easier). Two hundred ninety microliters of the reservoir fluid was pipetted into each patch through the open side. The open side is then heat-sealed closed to contain the fluid.

Modified Franz vertical cells were used for in vitro skin permeation studies which were carried out to determine the burst effect. The release liner was peeled off the system and the foil impermeable backing was also removed immediately prior to placing the system on heat-separated human epidermis. The epidermis and patch were then mounted between the donor and receiver compartments and clamped in place. The receiver compartments were filled with phosphate buffer and the temperature was maintained at 32° C. Samples were taken at preset intervals and assayed by HPLC.

Figure 4:
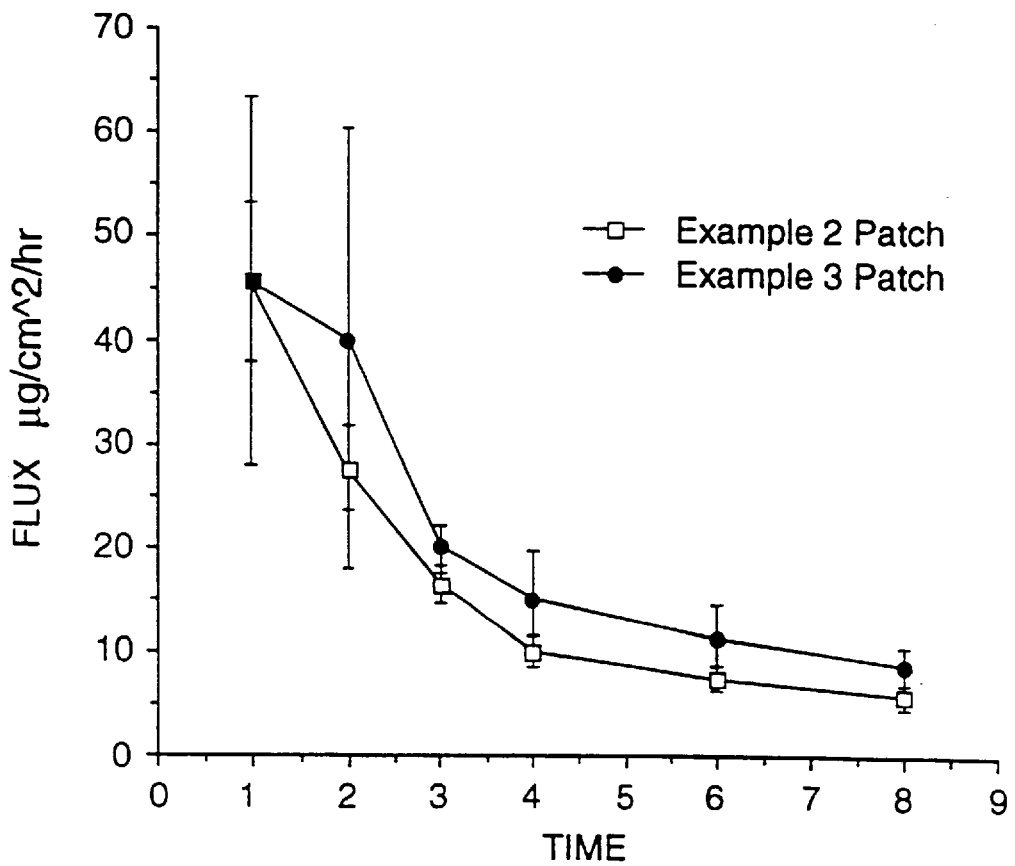

The results of these tests are shown in FIG. 4. For comparison purposes the flux from the device of Example 2 is included in FIG. 4.

EXAMPLE 4

A matrix or monolith reservoir type device in which the weight ratio of a binary solvent system is regulated by an overlying permeable layer was prepared as follows.

Polydimethylsiloxane (Dow Corning 4201) and a polyaminoacrylate (Plastoid E35H) in a 9:1 weight ratio combined with 0.5% or 1% dexmedetomidine were blended, cast onto a release liner layer and heated to 70° C. for 30 minutes to evaporate solvent. A permeable layer (Celgard microporous polypropylene or a nonwoven polyester) was placed on the cast film and a saturated solution of dexmedetomidine in a 4:1 by weight ethanol:PGML mixture was applied to the permeable layer. The amount of the solution was either 50% by weight or 100% by weight of the polymer blend. The assemblies were covered for 24 hr at ambient temperature to allow the solution to be absorbed into the polymer blend. The assemblies were then uncovered, the release liner stripped from the film, and the flux of dexmedetomidine from the resulting devices was determined as above.

Figure 6:
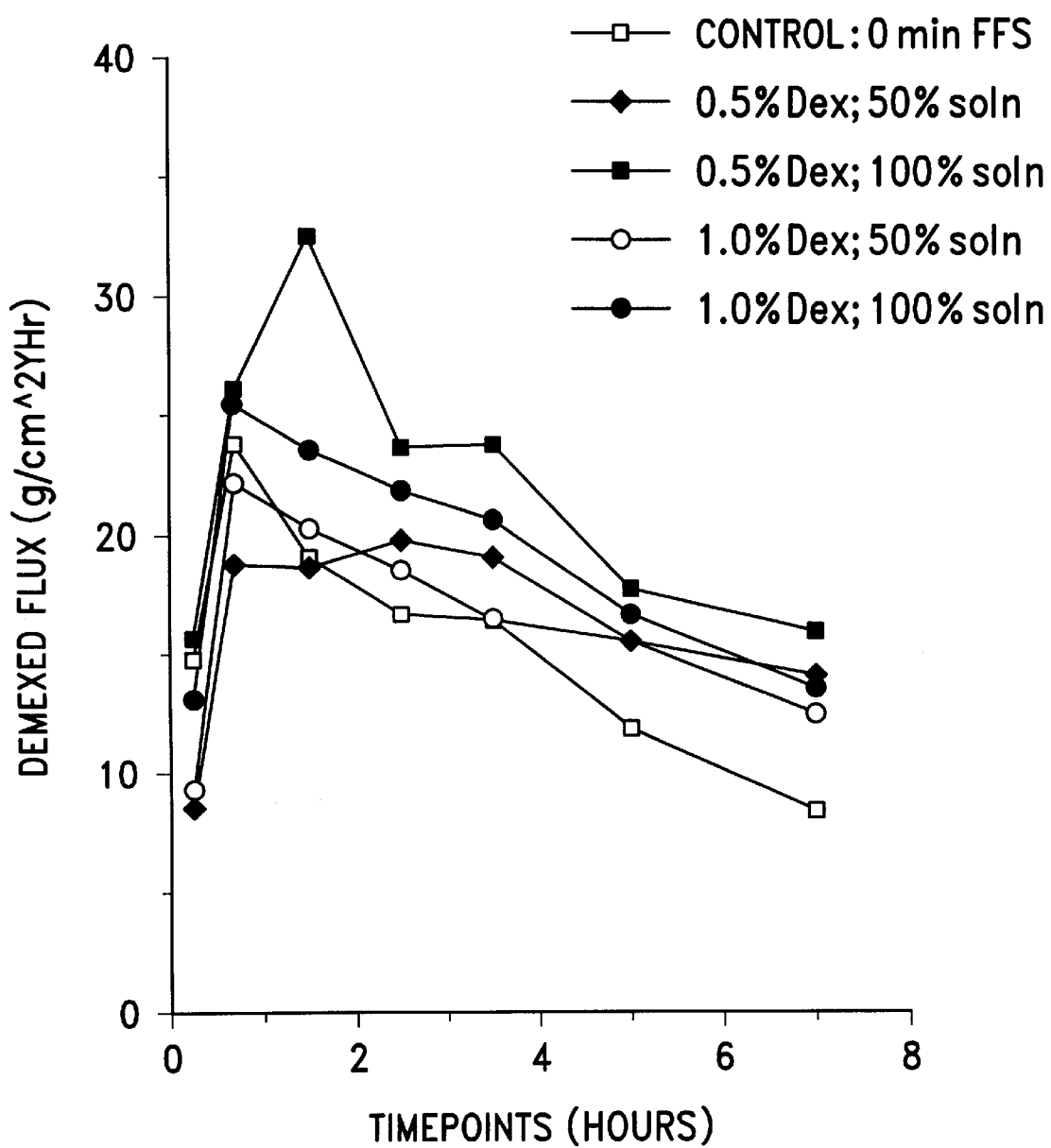
FIG. 6 is a graph showing the in vitro flux of dexmedetomidine versus teim as determined pursuant to Example 4 infra.

FIG. 6 shows the results of the flux tests.

Modifications of the above-described modes for carrying out the invention that are obvious to those of skill in the fields of chemistry, transdermal drug delivery, pharmacology, and related fields are intended to be within the scope of the following claims.

We claim:

1. A device for administering a drug through an area of intact skin over an administration period wherein the flux of drug through said area varies temporally in a controlled manner comprising:

(a) a multi-phase reservoir comprising a hydrophilic polymer and a hydrophobic polymer, said drug dissolved in a solvent mixture comprising a first solvent and a second solvent in a predetermined weight ratio, wherein at least one of the solvents is a skin permeation enhancer and said flux is a function of the weight ratio of the first solvent to the second solvent in the reservoir;

(b) a means for effecting controlled differential transport of one of said first and second solvents relative to the other from the reservoir during said administration period whereby the weight ratio of the first solvent to the second solvent in the reservoir is changed in a controlled manner and thus said flux is changed in a controlled manner; and (c) means for maintaining the device in drug and solvent transferring relationship with said area of skin.

2. The device of claim 1, wherein the first solvent is volatile, having a vapor pressure of greater than about 10 mm Hg at 25° C. and the second solvent is nonvolatile, having a vapor pressure of less than about 10 mm Hg at 25° C. and (b) comprises a a semi-permeable membrane overlying the reservoir that is permeable to the first solvent and regulates the rate at which the solvent evaporates from the reservoir during the administration period.

3. The device of claim 1 wherein the predetermined weight ratio is approximately the weight ratio at which the partitioning of the first and second solvents into the skin is at a maximum.

4. The device of claim 1 wherein the first solvent is ethanol and the second solvent is propylene glycol monolaurate and the predetermined weight ratio is approximately 4:1.

5. The device of claim 1 wherein the reservoir is in the form of a confined space in which the solution of drug in the first and second solvents is contained.

6. The device of claim 1 wherein the reservoir is in the form of a polymer matrix in which the solution of drug in the first and second solvents is dispersed.

7. The device of claim 1 wherein the solution of drug in the first and second solvents is associated with the hydrophilic polymer.

8. The device of claim 1 wherein (c) is an in-line layer of a pressure sensitive adhesive.

9. The device of claim 1 wherein (b) is a membrane which has pressure sensitive adhesive properties and constitutes the means for maintaining the device in drug and solvent transferring relationship with said area of skin.

10. A method for administering a drug transdermally through an area of intact skin over an administration period wherein the flux of drug through said area varies temporally in a controlled manner comprising:

(a) applying a formulation of the drug dissolved in a multi-phase reservoir comprising a hydrophilic polymer and a hydrophobic polymer, said drug dissolved in a solvent mixture comprising a first solvent and a second solvent in a predetermined weight ratio to the skin, wherein at least one of the solvents is a skin permeation enhancer and said flux is a function of the weight ratio of the first solvent to the second solvent in the reservoir; and (b) effecting controlled differential transport of one of said first and second solvents relative to the other from the reservoir during said administration period whereby the weight ratio of the first solvent to the second solvent in the reservoir is changed in a controlled manner and thus said flux is changed in a controlled manner.

11. A method for administering a drug transdermally wherein there is an initial pulse in the flux of the drug through the skin followed by a substantially lower flux of drug through the skin comprising:

(a) applying a formulation of the drug and a volatile solvent having a vapor pressure of greater than about 10 mm Hg at 25° C. and a nonvolatile solvent having a vapor pressure of less than about 10 mm Hg at 25° C. to the skin wherein at least one of the solvents is a skin permeation enhancer and the formulation is covered by a backing that is permeable to the volatile solvent said drug further dissolved in a multi-phase reservoir comprising a hydrophilic polymer and a hydrophobic polymer; and (b) permitting the volatile solvent to evaporate from said formulation through said backing whereby the magnitude and duration of the pulse is determined, at least in part, by the permeability of the backing to the volatile solvent.

12. The device of claim 1 wherein (b) comprises a semi-permeable membrane underlying the reservoir that is permeable to the first and second solvents but to a varying degree and regulates the rates at which the first and second solvents diffuse from the reservoir to the skin.

13. The device of claim 2 wherein (b) further comprises a semi-permeable membrane underlying the reservoir that is permeable to the first and second solvents but to a varying degree and regulates the rates at which the first and second solvents diffuse from the reservoir to the skin.

14. The device of claim 1 wherein the solvent mixture is non-aqueous.

15. A device for administering a drug through an area of intact skin over an administration period wherein the flux of drug through said area varies temporally in a controlled manner comprising:

(a) a reservoir comprising said drug dissolved in a solvent mixture comprising a first solvent and a second solvent in a predetermined weight ratio, wherein at least one of the solvents is a skin permeation enhancer and said flux is a function of the weight ratio of the first solvent to the second solvent in the reservoir;

(b) means for effecting controlled differential transport of one of said first and second solvents relative to the other from the reservoir during said administration period whereby the weight ratio of the first solvent to the second solvent in the reservoir is changed in a controlled manner and thus said flux is changed in a controlled manner; and (c) means for maintaining the device in drug and solvent transferring relationship with said area of skin.

16. The device of claim 15 wherein the first solvent is volatile having a vapor pressure of greater than about 10 mm Hg at 25° C. and the second solvent is nonvolatile having a vapor pressure of less than about 10 mm Hg at 25° C. and (b) comprises a semi-permeable membrane overlying the reservoir that is permeable to the first solvent and regulates the rate at which the solvent evaporates from the reservoir during the administration period.

17. The device of claim 15 wherein (b) comprises a semi-permeable membrane underlying the reservoir that is permeable to the first and second solvents but to a varying degree and regulates the rates at which the first and second solvents diffuse from the reservoir to the skin.

18. The device of claim 16 wherein (b) further comprises a semi-permeable membrane underlying the reservoir that is permeable to the first and second solvents but to a varying degree and regulates the rates at which the first and second solvents diffuse from the reservoir to the skin.

19. The device of claim 15 wherein the predetermined weight ratio is approximately the weight ratio at which the partitioning of the first and second solvents into the skin is at a maximum.

20. The device of claim 15 wherein the first solvent is ethanol and the second solvent is propylene glycol monolaurate and the predetermined weight ratio is approximately 4:1.

21. The device of claim 15 wherein the reservoir is in the form of a confined space in which the solution of drug in the first and second solvents is contained.

22. The device of claim 15 wherein the reservoir is in the form of a polymer matrix in which the solution of drug in the first and second solvents is dispersed.

23. The device of claim 22 wherein the polymer matrix is comprised of a mixture of a hydrophobic polymer and a hydrophilic polymer.

24. The device of claim 23 wherein the solution of drug in the first and second solvents is associated with the hydrophilic polymer.

25. The device of claim 24 wherein the solvent mixture is non-aqueous.

26. The device of claim 15 wherein (c) is an in-line layer of a pressure sensitive adhesive.

27. The device of claim 17 wherein the semi-permeable membrane has pressure sensitive adhesive properties and constitutes the means for maintaining the device in drug and solvent transferring relationship with said area of skin.

28. A method for administering a drug transdermally through an area of intact skin over an administration period wherein the flux of drug through said area varies temporally in a controlled manner comprising:

(a) applying a formulation of the drug dissolved in a solvent mixture comprising a first solvent and a second solvent in a predetermined weight ratio to the skin, wherein at least one of the solvents is a skin permeation enhancer and said flux is a function of the weight ratio of the first solvent to the second solvent; and (b) effecting controlled differential transport of one of the solvents relative to the other during the administration period whereby the weight ratio of the first solvent to the second solvent in the formulation is changed in a controlled manner and thus said flux is changed in a controlled manner.

29. A method of administering a drug transdermally wherein there is an initial pulse in the flux of the drug through the skin followed by a substantially lower flux of drug through the skin comprising:

(a) applying a formulation of the drug and a volatile solvent having a vapor pressure of greater than about 10 mm Hg at 25° C. and a nonvolatile solvent having a vapor pressure of less than about 10 mm Hg at 25° C. to the skin wherein at least one of the solvents is a skin permeation enhancer and the formulation is covered by a backing that is permeable to the volatile solvent;

(b) permitting the volatile solvent to evaporate from said formulation through said backing whereby the magnitude and duration of the pulse is determined at least in part by the permeability to the backing to the volatile solvent.

* * * * *